Figure 1A:
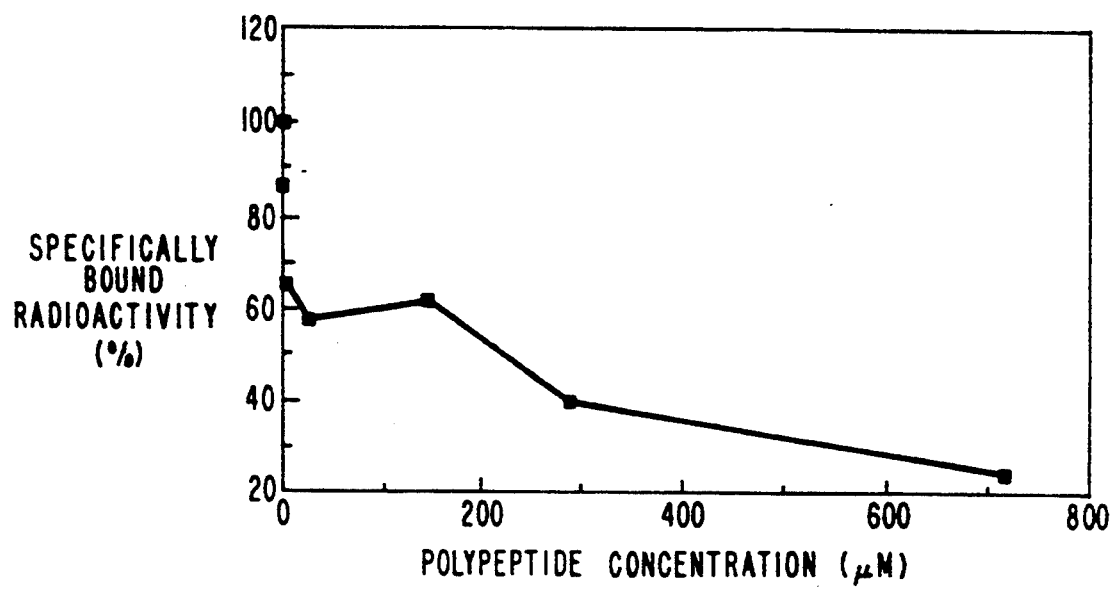

US005451658A

United States Patent [19]

Seelig

[11] Patent Number: 5,451,658

[45] Date of Patent: Sep. 19, 1995

[54] ANTAGONISTS OF HUMAN GAMMA INTERFERON

[75] Inventor: Gail F. Seelig, Watchung, N.J.

[73] Assignee: Schering Corporation, Kenilworth, N.J.

[21] Appl. No.: 30,077

[22] PCT Filed: Sep. 25, 1991

[86] PCT No.: PCT/US91/06771

§ 371 Date: Mar. 19, 1993

§ 102(e) Date: Mar. 19, 1993

[87] PCT Pub. No.: WO92/06115

PCT Pub. Date: Apr. 16, 1992

Related U.S. Application Data

[63] Continuation-in-part of Ser. No. 589,106, Sep. 27, 1990, abandoned.

[51] Int. Cl.[6] .......................... C07K 7/00; C07K 14/00

[52] U.S. Cl. .................................... 530/300; 530/324; 530/326; 530/351

[58] Field of Search ....................... 424/85.8; 435/70.4, 435/172.2, 240.27, 69.6, 69.1; 514/2; 530/351, 387.1, 387.2, 388.1, 388.23, 300, 324, 326

[56] References Cited

U.S. PATENT DOCUMENTS 4,727,138 2/1988 Goeddel et al. ....................... 536/27
4,731,237 3/1980 Reagen et al. ........................ 424/86

FOREIGN PATENT DOCUMENTS 0103898 3/1984 European Pat. Off. .... C07C 103/52
0122628 10/1984 European Pat. Off. ...... C12P 21/00
9102005 2/1991 WIPO .......................... C07K 15/26

OTHER PUBLICATIONS

Harris et al. Tibtech 11:42–44 (1993).
Lord et al. Mol. Immunol. 26:637–640 (1989).
Alfa et al. J. Immunol. 141:2474–2479 (1988).
Sikonska J. Biol Resp. Mod. 7:327–358 (1988).
Ashai Chem. Co. Chem. Abstracts 104:172 (1986) JP,A6041697.
G. Yuzo Chem. Abstracts 107:513 (1987) Hybridons 6:173781 (1987).
Ichimori et al., J. Immunol. Meth. 80:55 (1985).
Langer et al., Immunology Today 9:393 (1988).
Rose et al., Biochem. J. 215:273 (1983).
Seelig et al., Biochemistry 27:1981 (1988).
Seelig et al., J. Interferon Res. 9 (Suppl. 2):S184, Abstract A4–20 (1989).

*Primary Examiner*—David L. Lacey
*Assistant Examiner*—Phillip Gambel
*Attorney, Agent, or Firm*—Paul G. Lunn; Norman C. Dulak; James R. Nelson

[57] ABSTRACT

Novel synthetic polypeptides having amino acid sequences corresponding to the sequence of one or more specific regions of human gamma interferon are provided by this invention. These polypeptides specifically inhibit the binding of human gamma interferon to cellular receptors and the biological activity of such interferon. Antibody antagonists of the binding of human gamma interferon to cellular receptors based Upon the use of the polypeptides as antigens are also provided. Some of these antagonists bind to specific regions of gamma interferon which are believed to be involved in interactions between the intefferon and its receptors. Other antibody antagonists are anti-idiotypic antibodies which appear to compete directly with gamma interferon for binding to the cellular receptors. Also provided are methods for the use of the polypeptides and antibodies as inhibitors of the binding of gamma interferon to its cellular receptors.

1 Claim, 2 Drawing Sheets

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:

(A) LENGTH: 146 amino acids
(B) TYPE: amino acid
(D) TOPOLOGY: linear (ii) MOLECULE TYPE: peptide (xi) SEQUENCE DESCRIPTION: SEQ ID NO: 1:

| Cys | Tyr | Cys | Gln | Asp | Pro | Tyr | Val | Lys | Glu | Ala | Glu | Asn | Leu | Lys | Lys |
|---|---|---|---|---|---|---|---|---|---|---|---|---|---|---|---|
| 1 | | | | 5 | | | | | 10 | | | | | 15 | |

| Tyr | Phe | Asn | Ala | Gly | His | Ser | Asp | Val | Ala | Asp | Asn | Gly | Thr | Leu | Phe |
|---|---|---|---|---|---|---|---|---|---|---|---|---|---|---|---|
| | | | 20 | | | | | 25 | | | | | 30 | | |

| Leu | Gly | Ile | Leu | Lys | Asn | Trp | Lys | Glu | Glu | Ser | Asp | Arg | Lys | Ile | Met |
|---|---|---|---|---|---|---|---|---|---|---|---|---|---|---|---|
| | | 35 | | | | | 40 | | | | | 45 | | | |

| Gln | Ser | Gln | Ile | Val | Ser | Phe | Tyr | Phe | Lys | Leu | Phe | Lys | Asn | Phe | Lys |
|---|---|---|---|---|---|---|---|---|---|---|---|---|---|---|---|
| | 50 | | | | | 55 | | | | | 60 | | | | |

| Asp | Asp | Gln | Ser | Ile | Gln | Lys | Ser | Val | Glu | Thr | Ile | Lys | Glu | Asp | Met |
|---|---|---|---|---|---|---|---|---|---|---|---|---|---|---|---|
| 65 | | | | | 70 | | | | | 75 | | | | | 80 |

| Asn | Val | Lys | Phe | Phe | Asn | Ser | Asn | Lys | Lys | Lys | Arg | Asp | Asp | Phe | Glu |
|---|---|---|---|---|---|---|---|---|---|---|---|---|---|---|---|
| | | | | 85 | | | | | 90 | | | | | 95 | |

| Lys | Leu | Thr | Asn | Tyr | Ser | Val | Thr | Asp | Leu | Asn | Val | Gln | Arg | Lys | Ala |
|---|---|---|---|---|---|---|---|---|---|---|---|---|---|---|---|
| | | | 100 | | | | | 105 | | | | | 110 | | |

| Ile | His | Glu | Leu | Ile | Gln | Val | Met | Ala | Glu | Leu | Ser | Pro | Ala | Ala | Lys |
|---|---|---|---|---|---|---|---|---|---|---|---|---|---|---|---|
| | | 115 | | | | | 120 | | | | | 125 | | | |

| Thr | Gly | Lys | Arg | Lys | Arg | Ser | Gln | Met | Leu | Phe | Arg | Gly | Arg | Arg | Ala |
|---|---|---|---|---|---|---|---|---|---|---|---|---|---|---|---|
| | 130 | | | | | 135 | | | | | 140 | | | | |

| Ser | Gln |
|---|---|
| 145 | |

(2) INFORMATION FOR SEQ ID NO: 2:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO: 2:

| Lys | Lys | Tyr | Phe | Asn | Ala | Gly | Gly | Gly | Gly | Arg | Lys | Arg | Ser | Gln | Met |
|---|---|---|---|---|---|---|---|---|---|---|---|---|---|---|---|
| 1 | | | | 5 | | | | | 10 | | | | | 15 | |

Leu (2) INFORMATION FOR SEQ ID NO: 3:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO: 3:

| Arg | Lys | Arg | Ser | Gln | Met |
|---|---|---|---|---|---|
| 1 | | | | 5 | |

(2) INFORMATION FOR SEQ ID NO: 4:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO: 4:

```
Cys  Tyr  Cys  Gln  Asp  Pro  Tyr  Val  Lys
 1              5
```

( 2 ) INFORMATION FOR SEQ ID NO: 5:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 5:

```
Asp  Tyr  Val  Lys  Glu  Ala  Glu  Asn  Leu  Lys  Lys  Tyr  Phe  Asn
 1              5                             10
```

( 2 ) INFORMATION FOR SEQ ID NO: 6:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 6:

```
Leu  Ile  Gln  Val  Met  Ala  Glu  Leu  Ser  Pro  Ala  Ala  Lys  Thr  Gly
 1              5                             10                         15
```

( 2 ) INFORMATION FOR SEQ ID NO: 7:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 7:

```
Leu  Ser  Pro  Ala  Ala  Lys  Thr  Gly  Lys  Arg  Lys  Arg  Ser  Gln  Met
 1              5                             10                         15
```

( 2 ) INFORMATION FOR SEQ ID NO: 8:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 8:

```
Gly  Ile  Leu  Lys  Asn  Trp  Lys  Glu  Glu  Ser  Asp  Arg  Lys  Ile  Cys
 1              5                             10                         15
```

( 2 ) INFORMATION FOR SEQ ID NO: 9:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 9:

```
Val  Gln  Arg  Lys  Ala  Ile  His  Glu  Leu  Ile  Gln  Val  Met  Ala  Glu
 1              5                             10                         15
```

( 2 ) INFORMATION FOR SEQ ID NO: 10:

( i ) SEQUENCE CHARACTERISTICS:

(A) LENGTH: 32 amino acids
(B) TYPE: amino acid
(D) TOPOLOGY: linear (ii) MOLECULE TYPE: peptide (xi) SEQUENCE DESCRIPTION: SEQ ID NO: 10:

| Lys | Lys | Tyr | Phe | Asn | Ala | Gly | His | Ser | Asp | Val | Ala | Asp | Asn | Gly | Lys |
|---|---|---|---|---|---|---|---|---|---|---|---|---|---|---|---|
| 1 | | | | 5 | | | | | 10 | | | | | 15 | |

| Ala | Ile | His | Glu | Leu | Ile | Gln | Gly | Lys | Arg | Lys | Arg | Ser | Gln | Met | Leu |
|---|---|---|---|---|---|---|---|---|---|---|---|---|---|---|---|
| | | | 20 | | | | 25 | | | | | 30 | | | |

ANTAGONISTS OF HUMAN GAMMA INTERFERON

The present application is the United States national application corresponding to International Application No. PCT/US 91/06771, filed Sep. 25, 1991 and designating the United States, which PCT application is in turn a continuation-in-part of U.S. application Ser. No. 07/589,106, filed Sep. 27, 1990 the benefit of which applications are claimed pursuant to the provisions of 35 U.S.C. §§120,363 and 365 (C).

BACKGROUND OF THE INVENTION

Gamma interferon is a protein produced by activated helper T cells which manifests antiviral, antiproliferative and immunomodulatory activities. The antiviral and antiproliferative activities of gamma interferon are largely suppressive, while the immunomodulatory activity is primarily expressed through stimulation of a variety of immune functions, although the inhibition of immune function is also known to occur.

Although the mechanism by which gamma interferon exerts its effects on cells is not understood, it is known that it binds to specific cellular receptors [Langer et al, *Immunology Today* 9:393 (1988)]. Aguet et al. [Cell 55:273 (1988)]have cloned and sequenced a gene for a gamma interferon receptor. The molecular weight of the encoded protein deduced from the sequence is consistent with the molecular weight of a gamma interferon receptor recently isolated from human placenta [Calderon et al., *Proc. Natl. Acad. Sci. USA* 85:4837 (1988)].

Gamma interferon is believed to be involved in autoimmune disease. Elevated levels of gamma interferon are also believed to stimulate macrophages that erroneously digest myelin in the brain and spinal cord of multiple sclerosis (MS) sufferers.

Because gamma interferon acts at specific cellular receptors and is implicated in autoimmune disease and MS, agents which could inhibit the binding of such interferon to its cellular receptors would be useful therapeutically.

SUMMARY OF THE INVENTION

This invention provides novel polypeptides containing up to 50 amino acid residues and comprising one or more amino acid subsequences selected from the group consisting of the subsequences defined by amino acid residues 15-21 and 132-137 of the sequence defined by SEQ ID NO:1. Preferably the polypeptides contain up to 40, and more preferably up to 35, amino acid residues.

In some polypeptides comprising both of the subsequences, the subsequences are separated by a peptide linker containing from 1 to about 20 amino acid residues. In other polypeptides comprising both subsequences, the subsequences are in two separate polypeptides joined by disulfide bridges.

This invention further provides antibodies against polypeptides containing up to 50, preferably up to 40 and more preferably up to 35, amino acid residues and comprising one or more amino acid subsequences selected from the group consisting of the subsequences defined by amino acid residues 15–21 and 132–137 of the sequence defined by SEQ ID NO:1, which antibodies are characterized by an ability to specifically bind to the polypeptides and to human gamma interferon and to inhibit the binding of such interferon to cellular receptors.

The present invention still further provides anti-idiotypic antibodies against the above-mentioned antibodies. These anti-idiotypic antibodies also inhibit the binding of human gamma interferon to cellular receptors.

All of the antibodies of this invention can be either polyclonal antibodies from an antiserum, or monoclonal antibodies. Binding fragments made from such antibodies and humanized or otherwise engineered antibodies are also a part of this invention.

Also provided are methods for using the foregoing polypeptides and antibodies to inhibit the binding of such interferon to cellular receptors.

One method comprises contacting cells bearing receptors for human gamma interferon with an effective amount of a polypeptide containing up to 50, preferably up to 40 and more preferably up to 35, amino acid residues and comprising one or more amino acid subsequences selected from the group consisting of the subsequences defined by amino acid residues 15–21 and 132–137 of the sequence defined by SEQ ID NO:1.

Another method comprises contacting human gamma interferon with an effective amount of an antibody which specifically binds to human gamma interferon and to a polypeptide containing up to 50, preferably up to 40 and more preferably up to 35, amino acid residues and comprising one or more amino acid subsequences selected from the group consisting of the subsequences defined by amino acid residues 15–21 and 132–137 of the sequence defined by SEQ ID NO:1.

Still another method comprises contacting cells bearing receptors for human gamma interferon with an effective amount of a first anti-idiotypic, antibody against a second antibody, which second antibody specifically binds to human gamma interferon and to a polypeptide containing up to 50, preferably up to 40 and more preferably up to 35, amino acid residues and comprising one or more amino acid subsequences selected from the group consisting of the subsequences defined by amino acid residues 15–21 and 132–137 of the sequence defined by SEQ ID NO:1.

In addition to their use as therapeutic agents, the polypeptides, antibodies and methods of the present invention are useful for the in vitro study of the mechanism of gamma interferon binding to various cell types and for sceening for other gamma interferon antagonists or agonists.

BRIEF DESCRIPTION OF THE FIGURES

This invention can be more readily understood by reference to the accompanying figures, in which:

FIGS. 1A and 1B are graphical representations of the inhibition of the binding of $^{125}$I-labeled human gamma interferon D to Daudi cells by polypeptides having amino acid sequences defined by SEQ ID NO:2 (FIG. 1A) and by SEQ ID NO:3 (FIG 1B). Percent specifically bound radioactivity is shown in both panels as a function of polypeptide concentration.

FIG. 2 is a graphical representation of the inhibition of the binding of $^{125}$I-labeled human gamma interferon D to Daudi cells by antiserum against the polypeptide showing percent specifically bound radioactivity as a function of the amount of antiserum.

FIG. 3 is a graphical representation of the inhibition by a polypeptide having an amino acid sequence defined by SEQ ID NO:10 of the induction of class II major histocompatibility antigens on COLO-205 cells by recombinant human gamma interferon D. Percent inhibition is shown as a function of polypeptide concentration in the presence of a constant 150 pM concentration of interferon.

DESCRIPTION OF THE INVENTION

All references cited herein are hereby incorporated in their entirety by reference. All amino acid sequences disclosed follow the normal convention, with the amino terminus on the left and the carboxyl terminus on the right. Standard three-letter abbreviations are used for the amino acid residues in the sequences (37 C.F.R. § 1.822). As used herein, "Aib" represents either 2- or 3-aminoisobutyric acid.

In the course of a search for specific inhibitors of human gamma interferon, it has surprisingly been found that certain polypeptides having amino acid sequences corresponding to the sequences of residues in specific regions of intact mature human gamma interferon are potent inhibitors of the binding of gamma interferon to its cellular receptors. The antagonistic actions of these polypeptides have been demonstrated in a radioligand-receptor assay system employing the polypeptides, $^{125}$I-labeled human gamma interferon and cells bearing specific receptors for such interferon. This invention provides such polypeptides.

The present invention also provides antibodies which inhibit the binding of human gamma interferon to cellular receptors by (a) combining with a region(s) in such interferon that apparently is involved in interactions with the receptors or by (b) mimicking gamma interferon itself, thereby competing with it for binding to the receptors. As a result, they also inhibit the biological activity of the interferon.

As used herein, human "gamma interferon" means a protein which (a) has an amine acid sequence substantially identical to the sequence of mature human gamma interferon A as defined in the Sequence Listing by SEQ ID NO:1 and (b) has biological activity that is common to native gamma interferon.

For convenience, the amine acid sequences of polypeptides mentioned below may be described in terms of the corresponding sequences of residues in the amine acid sequence of mature human gamma interferon defined by SEQ ID NO:1, with 1 being the amine-terminal cysteine residue and 146 being the carboxyl-terminal glutamine residue, etc.

Substantial identity of amine acid sequences means that the sequence of another gamma interferon compared to the sequence defined by SEQ ID NO:1 is identical or differs by one or more amine acid alterations (deletions, additions, substitutions) that do not substantially impair biological activity. For example, gamma interferon D, which lacks the first three amine-terminal residues (Cys-Tyr-Cys) of the interferon defined by SEQ ID NO:1, is substantially identical in the context of this invention. So too are the natural human gamma interferens which lack such amine-terminal residues and in addition display microheterogeneity at the carboxyl terminus [Seelig et al., *Biochemistry* 27:1981 (1988)].

As explained above, the polypeptides of the invention comprise one or more amine acid subsequences selected from the group consisting of the subsequences defined by amine acid residues 15–21 and 132–137 of the sequence defined by SEQ ID NO:1. Preferred polypeptides comprise both. These two subsequences comprise important "core regions" of human gamma interferon which are believed to be somehow involved in the receptor binding and/or biological activity of such interferon. The polypeptides may contain, in addition to these core regions, additional flanking sequences comprising amino acid residues having sequences corresponding to the sequences of residues flanking the core regions in human gamma interferon.

For example, a preferred polypeptide having an amino acid sequence defined by SEQ ID NO:10 comprises two subsequences, one of which is defined by the sequence of amino acid residues 15–29 of SEQ ID NO:1. The other subsequence in this polypeptide is defined by the sequence of amino acid residues 130–138 of SEQ ID NO:1.

When the polypeptides of the invention contain both of the core regions (with or without additional flanking sequences), the regions are brought into proximity with each other in one of two ways. In a preferred embodiment, they are covalently joined in peptide linkage by an intervening linker peptide. This linker peptide can contain from 1 to about 20 amino acid residues, preferably from about 3 to about 8 residues. The amino acid residues selected for the linker peptide can be randomly selected from any of the 22 commonly known amino acids, although amino acid residues selected from the group consisting of Gly, Ala, Aib, Leu and Ile are preferred for use in random-sequence linkers.

Instead of randomly-selected amino acid residues, the linker peptide may contain from 1 to about 20, preferably from about 3 to about 8, residues having a sequence corresponding to the sequence of a subsequence of residues present in human gamma interferon between the two core regions. For example, in the preferred embodiment defined by SEQ ID NO:10, the two regions are joined by a peptide linker having a sequence corresponding to the sequence of residues 11–118 of SEQ ID NO:1.

The linker peptide is provided to confer flexibility on the molecule, so that the regions related to the interferon sequences may have a spatial relationship which approximates the spatial relationship of the corresponding sequences in intact human gamma interferon. It will of course be appreciated by those skilled in the art that this objective can also be accomplished with linkers comprising units other than amino acid residues. For example, many of the well-known linkers commonly employed in affinity chromatography can be used instead, as long as the flexibility and length of the linkers are similar to those of the polypeptide linkers. Such functionally equivalent, alternative linkers can be attached to the polypeptide segments of the molecules by known methods.

The order of the core regions (with or without additional flanking sequences) in the foregoing polypeptides is not essential. The region located in the amino-terminal region of human gamma interferon can be at the amino terminus of the polypeptide, or vice versa, although the former arrangement is preferred.

Some preferred polypeptides containing one or both of the core regions have amino acid sequences defined in the Sequence Listing by SEQ ID NOs. 2, 3 and 10.

In an alternative embodiment, the two core regions (with or without additional flanking sequences) can be brought into proximity by using two polypeptides, each of which contains one of the core regions. This is accomplished by incorporating cysteine residues into each of the polypeptides in regions outside of the core regions, and joining the polypeptides by disulfide bonds.

As used herein, the term "polypeptide" is defined to mean both embodiments in which the core regions are brought into proximity via a linker peptide, and those in which two polypeptide chains are joined by disulfide bridges.

Although the polypeptides of the invention contain only a relatively small number of amino acid residues compared to the total number of residues in mature human gamma interferon, they are nevertheless specific competitive inhibitors of the binding of the intact interferon to cellular receptors. As shown below, as much as 80% of the specific binding of $^{125}$I-labeled human gamma interferon D to Daudi cells can be abolished by such polypeptides.

It must be stressed that the polypeptides of the invention will bind to any cells which have gamma interferon receptors, such as B cells, T cells, eosinophils, smooth muscle cells, promyelocytes, macrophages, erythroid cells, monocytes and granulocytes. Daudi cells, a well-characterized B lymphoblast cell line derived from a Burkitt lymphoma patient which are available from the American Type Culture Collection under Accession No. CCL 213, are used below merely as a convenient way to demonstrate the inhibition of the binding of $^{125}$I-labeled gamma interferon to cellular receptors. Other cell lines can also be used for this purpose, such as the U-937 human histiocytic lymphoma line (ATCC CRL 1593).

The polypeptides are synthesized by a suitable method such as by exclusive solid phase synthesis, partial solid phase methods, fragment condensation or classical solution synthesis. The polypeptides are preferably prepared by solid phase peptide synthesis as described by Merrifield, *J. Am. Chem. Soc.* 85:2149 (1963). The synthesis is carried out with amino acids that are protected at the alpha-amino terminus. Trifunctional amino acids with lablie side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aromatic urethane type protecting groups [e.g., benzyloxycarbonyl (Cbz), substituted benzyloxycarbonyl and 9-fluorenylmethyloxycarbonyl (Fmoc)], aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). The preferred protecting group is Boc. The side-chain protecting groups for Tyr include tetrahydropyranyl, tert.-butyl, trityl, benzyl, Cbz, 4-Br-Cbz and 2,6-dichlorobenzyl. The preferred side-chain protecting group for Tyr is 2,6-dichlorobenzyl. The side-chain protecting groups for Asp include benzyl, 2,6-dichlorobenzyl, methyl, ethyl and cyclohexyl. The preferred side-chain protecting group for Asp is cyclohexyl. The side-chain protecting groups for Thr and Ser include acetyl, benzoyl, trityl, tetrahydropyranyl, benzyl, 2,6-dichlorobenzyl and Cbz. The preferred protecting group for Thr and Ser is benzyl. The side-chain protecting groups for Arg include nitro, Tos, Cbz, adamantyloxycarbonyl and Boc. The preferred protecting group for Arg is Tos. The side-chain amino group of Lys may be protected with Cbz, 2-Cl-Cbz, Tos or Boc. The 2-Cl-Cbz group is the preferred protecting group for Lys.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished polypeptide.

Solid phase synthesis is usually carried out from the carboxy-terminus by coupling the alpha-amino protected (side-chain protected) amino acid to a suitable solid support. An ester linkage is formed when the attachment is made to a chloromethyl or hydroxymethyl resin, and the resulting polypeptide will have a free carboxyl group at the C-terminus. Alternatively, when a benzhydrylamine or p-methylbenzhydrylamine resin is used, an amide bond is formed and the resulting polypeptide will have a carboxamide group at the C-terminus. These resins are commercially available, and their preparation has described by Stewart et al., "Solid Phase Peptide Synthesis" (2nd Edition), Pierce Chemical Co., Rockford, Ill., 1984.

The C-terminal amino acid, protected at the side chain if necessary and at the alpha-amino group, is coupled to the benzhydrylamine resin using various activating agents including dicyclohexylcarbodiimide (DCC), N,N'-diisopropylcarbodiimide and carbonyldiimidazole. Following the attachment to the resin support, the alpha-amino protecting group is removed using trifluoroacetic acid (TFA) or HCl in dioxane at a temperature between 0° and 25° C. Dimethylsulfide is added to the TFA after the introduction of methionine (Met) to suppress possible S-alkylation. After removal of the alpha-amino protecting group, the remaining protected amino acids are coupled stepwise in the required order to obtain the desired sequence.

Various activating agents can be used for the coupling reactions including DCC, N,N'-diisopropyl-carbodiimide, benzotriazol- 1 -yl-oxy-tris-(dimethylamino)-phosphonium hexafluorophosphate (BOP) and DCC-hydroxybenzotriazole (HOBt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction is monitored at each stage, e.g., by the ninhydrin reaction as described by Kaiser et al., *Anal. Bichem.* 34:595 (1970). In cases where incomplete coupling is found, the coupling reaction is repeated. The coupling reactions can be performed automatically with commercially available instruments.

After the entire assembly of the desired polypeptide, the polypeptide-resin is cleaved with a reagent such as liquid HF for 1-2 hours at 0° C., which cleaves the polypeptide from the resin and removes all side-chain protecting groups. A scavenger such as anisole is usually used with the liquid HF to prevent cations formed during the cleavage fom alkylating the amino acid residues present in the polypeptide. The polypeptide-resin may be deprotected with TFA/dithioethane prior to cleavage if desired.

Side-chain to side-chain cyclization on the solid support requires the use of an orthogonal protection scheme which enables selective cleavage of the side-chain functions of acidic amino acids (e.g., Asp) and the basic amino acids (e.g., Lys). The 9-fluorenylmethyl (Fm) protecting group for the side-chain of Asp and the 9-fluorenylmethyloxycarbonyl (Fmoc) protecting group for the side-chain of Lys can be used for this purpose. In these cases, the side-chain protecting groups of the Boc-protected polypeptide-resin are selectively removed with piperidine in DMF. Cyclization is achieved on the solid support using various activating agents including DCC, DCC/HOBt or BOP. The HF reaction is carried out on the cyclized polypeptide-resin as described above.

Recombinant DNA methodology can also be used to prepare the polypeptides. The known genetic code, tailored if desired for more efficient expression in a given host organism, can be used to synthesize oligonucleotides encoding the desired amino acid sequences. The phosphoramidite solid support method of Matteucci et al. [J. Am. Chem. Soc. 103:3185 (1981)], the method of Yoo et al. [J. Biol. Chem. 764:17078 (1989)], or other well known methods can be used for such synthesis. The resulting oligonucleotides can be inserted into an appropriate vector and expressed in a compatible host organism.

The polypeptides of the invention can be purified using HPLC, gel filtration, ion exchange and partition chromatography, countercurrent distribution or other known methods.

Antibodies can be prepared against the polypeptides of the invention using standard methods. As used herein, the word "antibody" refers to both polyclonal and monoclonal antibodies.

The polyclonal antibodies can be produced by immunizing a host animal such as a rabbit, rat, goat, sheep, mouse, etc. with one of the polypeptides. Preferably, one or more booster injections are given after the initial injection, to increase the antibody titer. Blood is then drawn from the animal and serum is prepared and screened by standard methods such as enzyme-linked immunosorbent assay (ELISA) using the polypeptide as the antigen.

Preferably, the immunogenicity of the polypeptides is increased by combination with an adjuvant and/or by conversion to a larger form prior to immunization.

Suitable adjuvants for the vaccination of animals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecyl-ammonium bromide, N,N-dioctadecyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

The immunogenicity of the polypeptides can also be enhanced by cross-linking or by coupling to an immunogenic carrier molecule (i.e., a macromolecule having the property of independently eliciting an immunological response in a host animal, to which the polypeptides of the invention can be covalently linked). Cross-linking or conjugation to a carrier molecule may be required because small polypeptides sometimes act as haptens (molecules which are capable of specifically binding to an antibody but incapable of eliciting antibody production, i.e., they are not immunogenic). Conjugation of such polypeptides to an immunogenic carrier molecule renders the fragments immunogenic through what is commonly known as the "carrier effect".

Suitable carrier molecules include, e.g., proteins and natural or synthetic polymeric compounds such as polypeptides, polysaccharides, lipopolysaccharides etc. A useful carrier is a glycoside called Quil A. which has been described by Morein et al., Nature 308:457 (1984). Protein carrier molecules are especially preferred, including but not limited to keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the polypeptides are to be elicited.

Covalent coupling to the carrier molecule can be carried out using methods well known in the art, the exact choice of which will be dictated by the nature of the carrier molecule used. When the immunogenic carrier molecule is a protein, the polypeptides of the invention can be coupled, e.g., using water soluble carbodiimides such as dicyclohexylcarbodiimide or glutaraldehyde.

Coupling agents such as these can also be used to cross-link the polypeptides to themselves without the use of a separate carrier molecule. Such cross-linking into aggregates can also increase immunogenicity.

Serum produced from animals thus immunized can be used directly. Alternatively, the IgG fraction can be separated from the serum using standard methods such as plasmaphoresis or adsorption chromatography using IgG-specific adsorbents such as immobilized Protein A.

Monoclonal antibodies can be prepared using standard methods, e.g., as described by Kohler et al. [Nature 256:495 (1975); Eur. J. Immunol. 6:511 (1976)]. Essentially, an animal is immunized as described above to produce antibody-secreting somatic cells. These cells are then removed from the immunized animal for fusion to myeloma cells.

Somatic cells with the potential to produce antibodies, particularly B cells, are suitable for fusion with a myeloma cell line. These somatic cells may be derived from the lymph nodes, spleens and peripheral blood of primed animals.

Specialized myeloma cell lines have been developed from lymphocytic tumors for use in hyridoma-producing fusion procedures [Kohler and Milstein, Eur. J. Immunol. 6:511 (1976); Shulman et al., Nature 276:269 (1978); Volk et al., J. Virol. 42:220 (1982)]. These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumor cells to produce their own antibodies. The purpose of using monoclonal techniques is to obtain fused hybrid cell lines with unlimited life spans that produce the desired single antibody under the genetic control of the somatic cell component of the hybridoma. To eliminate the production of tumor cell antibodies by the hybridomas, myeloma cell lines incapable of producing light or heavy immunoglobulin chains or deficient in antibody secretion mechanisms are used. A third reason for selection of these cell lines is for their suitability and efficiency for fusion.

Many myeloma cell lines may be used for the production of fused cell hybrids, including, e.g., P3X63-Ag8, P3/NS1-Ag4-1 (NS-1), Sp2/0-Ag14 and S194/5.XXO.-Bu.1. The P3X63-Ag8 and NS-1 cell lines have been described by Kohler and Milstein [*Eur. J. Immunol.* 6:511 (1976)]. Shulman et al. [*Nature* 276:269 (1978)]developed the Sp2/O-Ag14 myeloma line. The S 194/5.XXO.Bu. 1 line was reported by Trowbridge [*J. Exp. Med.* 148:313 (1979)].

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described by Kohler and Milstein, supra, Gefter et al. [*Somatic Cell Genet.* 3:231 (1977)], and Volk et al. (*J. Virol.* 42:220 (1982)]. The fusion-promoting agents used by those investigators were Sendai virus and polyethylene glycol (PEG).

Because fusion procedures produce viable hybrids at very low frequency (e.g., when spleens are used as a source of somatic cells, only one hybrid is obtained for roughly every $1 \times 10^5$ spleen cells), it is essential to have a means of selecting the fused cell hybrids from the remaining unfused cells, particularly the unfused myeloma cells. A means of detecting the desired antibody-producing hybridomas among other resulting fused cell hybrids is also necessary.

Generally, the selection of fused cell hybrids is accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused Cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques which have been described in the literature [see, e.g., Kennet et al. (editors), Monoclonal Antibodies and Hybridomas: A New Dimension in Biological Analyses, pp. 376–384, Plenum Press, New York (1980)].

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumors that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation.

The anti-idiotypic antibodies of the invention are directed against antibodies specific for the gamma interferon antigenic determinants present in some of the polypeptides of the invention. Such anti-idiotypic antibodies mimic or act like the original antigenic determinants (see, e.g., U.S. Pat. No. 4,731,237 to Reagan et al.). Like gamma interferon itself, these antibodies are presumed to bind specifically and directly to gamma interferon receptors.

Such anti-idiotypic antibodies are prepared by vaccinating an animal with an antibody (polyclonal or monoclonal) against a polypeptide of the invention. They may be recovered as a whole polyclonal antiserum or as an IgG or other fraction thereof, or as monoclonal antibodies produced by cloned hybridomas, as described above.

The antagonistic effects of the polypeptides and antibodies of this invention can readily be demonstrated by routine experimentation using the Daudi cell radioligand-receptor assay system described below. Recombinant human gamma interferon which can be used in this system can be made by standard recombinant methods and is also available commercially, e.g., from Genzyme Corp., Boston, Mass. Such interferon can readily be labeled with iodine-125 using, e.g., the lactoperoxidase method [David et al., *Biochemistry* 13:1014 (1974)] or the method of Bolton et al. [*Biochem. J.* 133:529 (1973)].

The present invention also encompasses binding fragments of the above-mentioned polyclonal and monoclonal antibodies, such as Fab, F(ab')$_2$, Fv fragments etc. Such fragments are obtained by conventional techniques including but not limited to papain or pepsin digestion of the intact antibodies. Of course, DNA prepared from hybridomas secreting the monoclonal antibodies of the invention can be manipulated using known recombinant DNA techniques to produce chimeric antibodies or fragments thereof. The antibodies can also be "humanized" as described by Verhoeyen et al. [*Science* 239:1534 (1988)], Reichmann et aL [*Nature* 332:323 (1988)] and Jones et al. [*Nature* 321:522 (1986)].

Pharmaceutical compositions can be prepared which contain effective amounts of one or more of the polypeptides or antibodies of the invention and a physiologically acceptable carrier. Such carriers are well known to those skilled in the art. The polypeptides and proteins can be administered directly or in the form of a composition to a human patient afflicted, e.g., by autoimmune disease, MS or another disease mediated by gamma interferon.

Determination of the proper dosage of a polypeptide or antibody of the invention for a particular situation is within the skill of the art. Generally, treatment is initiated with smaller dosages that are less than optimum. Thereafter, the dosage is increased by small increments until the optimum effect under the circumstances is reached. For convenience, the total daily dosage may be divided and administered in portions during the day if desired.

The amount and frequency of administration of the polypeptides and proteins-of the invention and the pharmaceutically acceptable salts thereof will be regulated according to the judgment of the attending clinician, taking into account such factors as age, condition and size of the patient and severity of the symptom(s) being treated.

EXAMPLES

Unless otherwise specified, percentages given below for solids in solid mixtures, liquids in liquids, and solids in liquids are on a wt/wt, vol/vol and wt/vol basis, respectively.

Protein Analysis

Protein determinations were carried out by the method of Lowry et al. [*J. Biol. Chem.* 193:265 (1951)]using bovine serum albumin as a standard.

Sources of Polypeptides and Proteins

Polypeptides having amino acid sequences corresponding to various regions of mature human gamma interferon A were synthesized using the solid-phase method of Merrifield [*J. Am. Chem. Soc.* 85:2149 (1963)]. The t-butyloxycarbonyl amino protecting group, symmetrical anhydrides, and an Applied Biosystems Model 430A solid-phase peptide synthesizer were employed. Following removal of protecting groups, the polypeptides were cleaved from the resin with hydrogen fluoride. Crude polypeptides recovered after cleavage from the resin were analyzed by reverse-phase HPLC in a Rainin Dynamax ® C-8 column (12 μ particle size, 300 Angstrom pore size, 4.6×250 mm).

In this way, the following polypeptides were prepared:

Lys-Lys -Tyr-Phe-Asn-Ala-Gly-Gly-Gly-Gly-Arg-Lys-Arg -Ser-Gln-Met-Leu (15-21-Gly-Gly-Gly-132-138; SEQ ID NO:2)

Arg-Lys-Arg-Ser-Gln-Met (132-137; SEQ ID NO:3)

Cys-Tyr-Cys-Gln-Asp-Pro-Tyr-Val-Lys (1-9; SEQ ID NO:4)

Asp-Tyr-Val-Lys-Glu-Ala-Glu-Asn-Leu-Lys-Lys -Tyr-Phe -Asn (Asp 7-19; SEQ ID NO:5)

Leu- Ile-Gln-Val-Met -Ala-Glu-Leu-Ser-Pro-Ala-Ala-Lys -Thr-Gly (116-130; SEQ ID NO: 6)

Leu -Ser-Pro-Ala-Ala-Lys-Thr-Gly-Lys-Arg-Lys-Arg-Ser -Gln-Met (123-137; SEQ ID NO:7)

Gly-Ile-Leu-Lys-Asn-Trp-Lys-Glu-Glu-Ser-Asp-Arg-Lys -Ile-Cys (34-47 Cys; SEQ ID NO:8)

Val-Gln-Arg-Lys-Ala-Ile-His-Glu-Leu-Ile-Gln-Val-Met -Ala-Glu (108-122; SEQ ID NO:9)

Lys-Lys-Tyr-Phe-Asn-Ala-Gly-His-Ser-Asp-Val-Ala-Asp -Asn-Gly-Lys-Ala-Ile-His-Glu-Leu-Ile-Gln-Gly-Lys -Arg-Lys-Arg-Ser-Gln-Met-Leu (15-29, 111-118, 130-138; SEQ ID NO:10)

The sequence of each polypeptide shown above is followed in parentheses by the corresponding human gamma interferon A residues (see SEQ ID NO:l) upon which the sequence was based, and the corresponding SEQ ID NO. assigned to the polypeptide in the Sequence Listing. Note that in some cases the sequences contain additional amino acid residues as indicated.

Recombinant human gamma interferons A and D were prepared and purified from transformed *E. coli,* essentially as described in U.S. Pat. No. 4,751,078.

PREPARATION OF ANTISERA

Anti-polypeptide Antibodies

Five-hundred μl volumes of aqueous pH 7.1 solutions containing 0.5 to 1.0 mg of the various polypeptides were emulsified with equal volumes of Freund's complete adjuvant and injected intradermally (0.1 ml per injected site) into New Zealand White rabbits (Hazelton Labs). Booster injections containing about 0.25 to 0.5 mg of polypeptide in Freund's incomplete adjuvant were administered at approximately 4-week intervals as required, as judged by ELISA analyses of serum samples using the polypeptides and gamma interferon as antigens.

Antibodies against the discontinous polypeptide were purified commercially by adsorption to a Protein A-Sepharose ® column equilibrated with 1.5M glycine buffer, pH 8.9. Analysis by SDS polyacrylamide gel electrophoresis [Laemmli, *Nature* 227:680 (1970)] showed that the antibody preparation thereby obtained was 95% pure IgG.

Anti-idiotypic Antibodies

The purified rabbit IgG antibodies against the discontinuous polypeptide were used to immunize Balb/c mice (Charles River Labs). The mice were primed intraperitoneally with 0.5 ml of pristane (Sigma Chemical Co., St. Louis, Mo.) 6 days prior to immunization by the same route with 87 μg of the IgG protein in 125 μl of phosphate buffered saline and 125 μl of Freund's complete adjuvant. Boosts of approximately 50 μg of the protein in 50% Freund's incomplete adjuvant were given at approximately 2-3 week intervals as needed, based upon ELISA analyses.

ELISA analysis of the rabbit antisera was carried out at room temperature. A 96-well microtiter plate (Nunc) was coated with 0.25 μg of antigen in 100 μl per well for 1 hour at room temperature. The plate was washed 5 times with tris-buffered saline (TBS), pH 7.5, containing 0.05% Tween 20 (polyoxethylenesorbitan monolaurate). The plate was blocked with 1% bovine serum albumin for 1 hour, washed 5-times with TBS and again washed 5 times with TBS.

The wells of the washed plate were coated with antisera to be tested for 1 hour, washed 5 times with TBS and coated with 2.5 mg of horseradish peroxidase-conjugated goat anti-rabbit IgG. Following incubation for 1 hour, the plate was washed 5 times with TBS and developed by adding either 2,2'-Azino-bis (3-ethylbenzthiazoline-6-sulfonic acid) (ABTS) or 3,3',5,5'-Tetramethylbenzidine (TMB) and hydrogen peroxide to each well. Color development was stopped after 10 minutes by adding a solution containing sulfuric acid (for TMB) or sodium dodecylsulfate (for ABTS), and the samples were read at 405 and 450 nm for ABTS and TMB, respectively, using a Molecular Devices ELISA reader.

ELISA analysis of mouse serum was performed in essentially the same way except that peroxidase-labeled goat anti-mouse IgG was used as the detection reagent.

Labeling of Human Recombinant Gamma Interferon

Recombinant human gamma interferon D was purified to homogeneity from an *E. coli* lysate essentially as described in U.S. Pat. No. 4,751,078, although similar interferon is available commercially from sources such as Genzyme Corp., Boston, Mass.

The interferon was labeled with iodine-125, essentially as described by Bolton et al. [*Biochem. J.* 133:529 (1973)], using $^{125}I$, Bolton-Hunter reagent from New England Nuclear, Boston, Mass. Briefly 2 mCi (2200 Ci/mmole) of Bolton-Hunter reagent (New England Nuclear, Boston, Mass.) in anhydrous benzene was dried by a gentle stream of nitrogen. Five micrograms of gamma interferon dissolved in 50 μl of 50 mM sodium phosphate buffer, pH 8.0, were added to the reaction vessel. The reaction was allowed to proceed for 2 hours at room temperature, after which unreacted Bolton-Hunter reagent was quenched with 50 μl of 1M glycine in 50 mM sodium phosphate, pH 8.0.

The radioiodinated protein was separated from unreacted labeling reagent by gel filtration in a 10 ml PD-10 Sephadex G-25® column (Pharmacia LKB Biotechnology, Piscataway, N.J.) equilibrated with 0.05M sodium phosphate buffer, pH 7.2, containing 0.5% gelatin. The same buffer was used to develop the column. One-ml fractions were collected, and aliquots were counted in a gamma counter. Labeled protein eluted in the column void volume (3–4 ml), while unreacted reagent eluted later (6–8 ml).

The labeled interferon typically had a specific radioactivity of 50 to 200 μC/μg. Analysis by SDS polyacrylamide gel electrophoresis followed by autoradiography showed that the labeled protein migrated as a single band with a mobility essentially identical to that of unlabeled gamma interferon.

Inhibition of the Binding of $^{125}I$-labeled Human Gamma Interferon D to Daudi Cells Daudi cell stock cultures were grown in RPMI 1640 medium containing 100 units/ml penicillin, 100 μg/ml streptomycin, 2 mM glutamine and 20% heat-inactivated fetal bovine serum. The cells were grown in T-75 flasks (50 ml/flask), seeded at $4\times10^5$ cells/ml and split at 2-day intervals (or seeded at 2.5×105 cells/ml for 3-day growth over weekends). The cultures were maintained during growth at 4° C.

The cells were harvested for assay by centrifugation at 300×g for 3 minutes at 4° C. The spent culture medium was discarded and the cell pellets were suspended in ice-cold binding buffer (RPMI 1640, 10% heat inactivated fetal bovine serum, 15 mM HEPES, 0.02% sodium azide). Cells were counted by hemocytometer, viability was established by percent trypan blue exclusion [Animal Cell Culture: A Practical Approach, 1986, R. I. Freshney (Ed.), IRL Press, LTD, pp. 76–77], and the cells were suspended at $\times10^6$ cells/ml in the cold binding buffer.

Binding assays were performed on polypeptides and rabbit antisera in 1-ml volumes using Sarstedt 1.5 ml screw cap conical tubes. All components were diluted in the cold binding buffer and added in the following order:

450 μl of unknown sample (or control binding buffer only)
50 μl of $^{125}I$-labeled gamma interferon D (105 cpm)
500 μl of cell suspension (106 viable cells)

In addition, 10 μl of an unlabeled gamma interferon A solution containing 1 μg of protein were added to some control tubes to determine the level of nonspecific binding by the labeled interferon. This amount of radioactivity was subtracted from all radioactivity measurements.

After all of the components had been added to each tube, the tubes were capped, inverted briefly to wet the entire inner surfaces and incubated for 2 hours in a cold room on an Adams Nutator® rocking platform. Following this incubation, the supernatant fluid was aspirated from each tube, taking care not to remove any cells.

One-hundred μl of the ice-cold binding buffer was added to each tube, and the pellets were suspended using a 200 μl Gilson Pipetman® and carefully layered atop 400 μl of ice-cold 5% sucrose in PBS in Sarstedt 600 μl conical tubes held in aluminum centrifugation racks. The samples were centrifuged at 1,000×g for 5 minutes at 4° C.

The supernatant fluids were carefully aspirated to avoid loss of cells, and the tubes were transferred to 12×75 mm tubes suitable for gamma counter use.

Binding Inhibition By Polypeptides

Figure 1B:
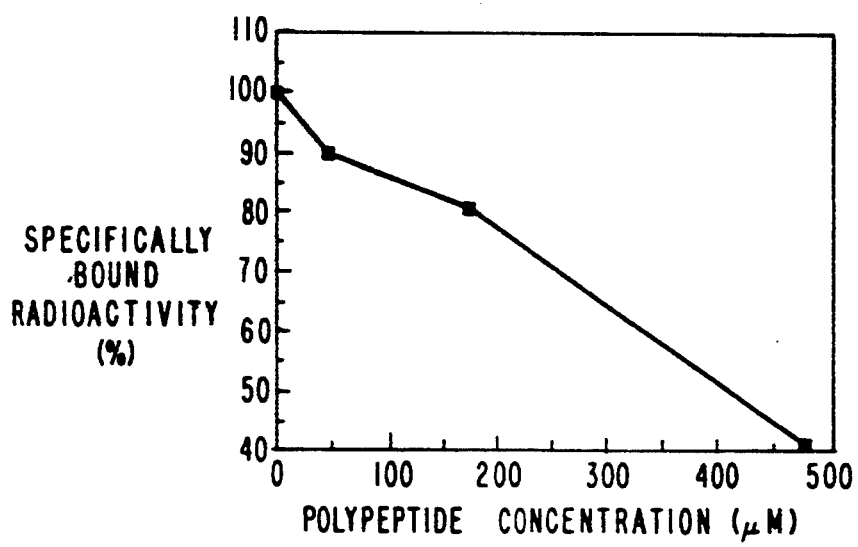

The polypeptides having amino acid sequences defined by SEQ ID NO:2 and SEQ ID NO:3 were tested in the receptor binding assay as described above, with the results shown in FIG. 1.

There, it can be seen that the polypeptide defined by SEQ ID NO:2 (panel A) and the other polypeptide (panel B) both inhibited the binding of $^{125}I$-labeled human gamma interferon D to receptors on Daudi cells. The former polypeptide was the more potent competitive inhibitor, showing binding inhibitions of about 15 and 35% at concentrations of 0.145 and 1.45 μM, respectively.

Binding Inhibition by Antibodies

Rabbit polyclonal antisera prepared against all of the polypeptides mentioned above were tested for ability to bind to the polypeptides and to human gamma interferon A and to inhibit the specific binding of human gamma interferon D to Daudi cells, with the results shown in Table I.

TABLE I

| | Characterization of Antisera | | |
|---|---|---|---|
| Polypeptide SEQ ID NO. | % $^{125}I$-Interferon Binding Inhibition[a] | Specific Polypeptide | Binding[b] to γ-Interferon A |
| 2 | 86 | + | + |
| 3 | — | – | – |
| 4 | 11 | + | – |
| 5 | 76 | + | + |
| 6 | 14 | + | – |
| 7 | 65 | + | + |
| 8 | 16 | + | +/– |
| 9 | 33 | + | + |

[a]Percent binding inhibitions are expressed as percentages of the specific binding shown by $^{125}I$-labeled human gamma interferon D in the absence of any inhibitor.
[b]Positive binding responses (+) were defined as ELISA results in which responses were more than 0.15 optical density (O.D.) units above background at. The +/– notation signifies responses that were between 0.0 and 0.15 O.D. units above background.

The data of Table I show that antibodies against polypeptides having amino acid sequences corresponding to the sequences of residues 7–19 (with an added N-terminal aspartate residue), 123–137 and 5–21/1-32–138 (with 3 bridging glycine residues) of mature human gamma interferon A (polypeptide SEQ ID NOs. 5, 7 and 2, respectively) were all antagonists of the specific binding of the labeled interferon to Daudi cell receptors. All three of these antisera contained antibodies that, as shown by ELISA, specifically bound to both the polypeptides against which they were produced and to gamma interferon A. No antibodies were produced against the 132–137 polypeptide (polypeptide SEQ ID NO:3), possibly because it was too small to be immunogenic unconjugated to a carrier molecule.

Figure 2:
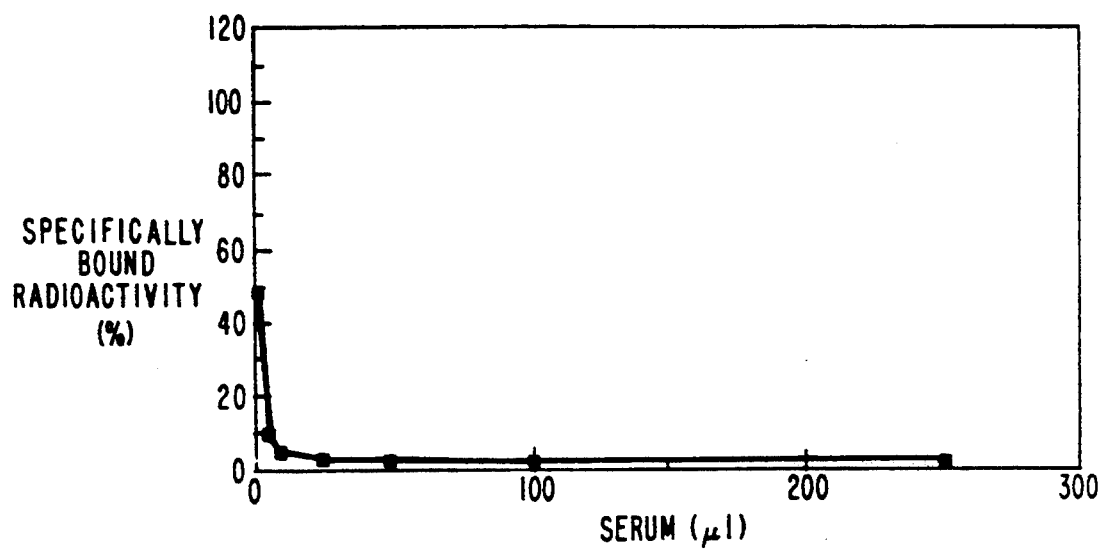

Rabbit preimmune serum was completely unreactive in all of the assays. As shown in FIG. 2, antiserum against the polypeptide defined by SEQ ID NO:2 almost completely abolished the specific binding of labeled gamma interferon D to Daudi cells at concentrations above about 25 μl of serum per ml of incubation mixture. About 50% binding inhibition was observed at a concentration of this antiserum of only 1 μl/ml.

The anti-idiotypic antiserum prepared using the IgG antibody fraction against the polypeptide defined by SEQ ID NO:2 also demonstrated significant receptor binding inhibition, as shown in Table II.

TABLE II

Inhibition of $^{125}$I-labeled Human Gamma Interferon Binding To Daudi Cells by Anti-idiotypic Antiserum

| Bleed[a] | % Specific Binding Inhibition[b] |
|---|---|
| first | 16 |
| first | 31 |
| first | 38 |
| second | 44 |

[a]The data shown are the results obtained using antiserum taken from mice immunized as described above 16 weeks after the first injection (first bleed) and 17 weeks thereafter (second bleed). The second bleeds of the three mice were pooled to produce the result shown.
[b]Results were normalized using control preimmune serum.

The data shown in Table II are the result of incubating 50-100 μl of mouse serum with $10^5$ cpm of the $^{125}$I-labeled gamma interferon and $1.5 \times 10^6$ viable Daudi cells, essentially as described above. The data show that the inhibitory ability of the antioidiotypic antiserum increased as the course of immunization progressed (i.e., the second bleed was stronger than the first).

Inhibition of the Biological Effects of Gamma Interferon

To demonstrate that the polypeptides of the invention also produce biological effects, the action of a representative polypeptide was observed in an interferon-responsive biological system.

Reagents and Cells

Recombinant human gamma interferon D having a specific activity of about $5 \times 10^6$ units/mg was prepared from transformed *E. coli* using standard methods.

COLO-205 cells (ATCC CLL 222) derived from a human adenocarcinoma were used to measure the induction by the interferon of class II major histocompatibility antigens (HLA-DR). The presence of the antigens on the cells was detected by Enzyme-Linked Immunosorbent Assay (ELISA) using a mouse monoclonal anti-HLA-DR antibody (Becton-Dickinson Catalog No. 7360) in conjunction with a peroxidate-labeled goat anti-mouse IgG. Color produced using 2,2'-Azinobis(3-Ethylbenzthiazoline-6-Sulfonic Acid) (ABTS; Kirkegaard & Perry Labs., Inc., Gaithersburg, Md.) was measured spectrophotometrically at 405 nm.

Inhibition of HLA-DR Induction

Bio-ELISA assay for HLA-DR induction by gamma interferon was carried out essentially as described by Gibson et al. [*J. Immunol. Meth.* 125:103 (1989)]. Briefly, COLO-205 cells were grown to confluence in T-75 flasks in RPMI 1640 medium containing 10% fetal calf serum (culture medium). The cells were trypsinized and seeded in 96-well tissue culture plates at a density of at least $10^5$ cells per well in 0.1 ml of culture medium. The cells were allowed to attach to the wells by overnight incubation at 37° C. in a 5% $CO_2$ incubator.

Control culture medium and various dilutions in culture medium of the polypeptide defined by SEQ ID NO:10 in the presence of a fixed 150 pM concentration of the interferon were added in a 0.1 ml volume to the wells and incubated for one hour at 37° C.

Following this incubation, the medium was removed from each well and the wells were washed three times with culture medium. Aliquots (0.1 ml) of culture medium were added to the wells, and the plates were incubated for 48 hours at 37° C. to allow for induction of HLA-DR antigen expression by interferon bound to the cells.

The wells were washed with 0.2 ml of phosphate buffered saline (PBS; 0.02M sodium phosphate, 0.15M NaCl, pH 7.4) and then fixed for two minutes with ice-cold anhydrous ethyl alcohol. The alcohol was removed, and the wells were washed once with 0.2 ml of PBS. Fifty microliters of a 1:50 dilution of the mouse monoclonal anti-HLA-DR antibody in PBS containing 0.5% bovine serum albumin were then added to each well, and the plates were incubated for one hour at room temperature.

Excess reagent was removed by washing the wells three times with 0.2 ml of PBS, after which 0.1 ml of a 1:5,000 dilution of peroxidase-labeled goat anti-mouse IgG was added to each well. The plates were incubated for one hour at room temperature. After washing each well three times with PBS as before, color was developed by the addition of ABTS for 5-10 minutes at room temperature. Absorbance was measured at 405 nm using an ELISA plate reader.

Figure 3:
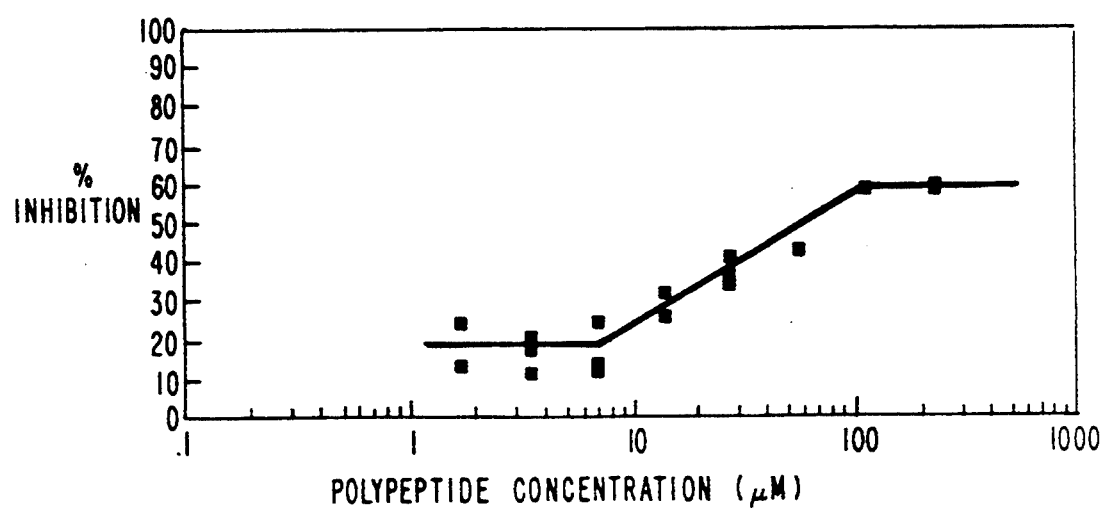

Results of an assay to measure inhibition of gamma interferon-induced HLA-DR expression in COLO-205 cells by the polypeptide defined by SEQ ID NO:10 are shown in FIG. 3. There, it can be seen that increasing concentrations of the polypeptide of from 7 to 100 μM produced progressively greater inhibition of antigen induction by the constant 150 pM concentration of interferon.

Many modifications and variations of this invention may be made without departing from its spirit and scope, as will become apparent to those skilled in the art. The specific embodiments described herein are offered by way of example only, and the invention is to be limited only by the terms of the appended claims.

What is claimed is:

1. A polypeptide which has an amino acid sequence selected from the group consisting of SEQ ID NO:2 and SEQ ID NO:10.

* * * * *